United States Patent
Hörndler et al.

(10) Patent No.: US 12,357,189 B2
(45) Date of Patent: Jul. 15, 2025

(54) METHOD AND DEVICE FOR OPERATING A MEDICAL IMAGING DEVICE FOR THE POSITIONALLY CORRECT REPRESENTATION OF NON-ANATOMICAL STRUCTURES DURING AN IMAGING EXAMINATION

(71) Applicant: Ziehm Imaging GmbH, Nuremberg (DE)

(72) Inventors: Klaus Hörndler, Nuremberg (DE); Marc Kachelriess, Nuremberg (DE); Michael Knaup, Reichenschwand (DE); Thomas König, Nuremberg (DE); Tim Vöth, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 152 days.

(21) Appl. No.: 17/816,247

(22) Filed: Jul. 29, 2022

(65) Prior Publication Data

US 2023/0032731 A1 Feb. 2, 2023

(30) Foreign Application Priority Data

Aug. 2, 2021 (DE) ..................... 10 2021 003 956.4

(51) Int. Cl.
*A61B 6/00* (2024.01)
*A61B 5/055* (2006.01)
*A61B 90/00* (2016.01)

(52) U.S. Cl.
CPC ............ *A61B 5/055* (2013.01); *A61B 6/4441* (2013.01); *A61B 90/36* (2016.02); *A61B 2090/364* (2016.02); *G06T 2207/10081* (2013.01)

(58) Field of Classification Search
CPC ............ G06T 2207/10081; A61B 6/12; A61B 2090/364; A61B 5/055; A61B 6/032;
(Continued)

(56) References Cited

U.S. PATENT DOCUMENTS

| | | | |
|---|---|---|---|
| 2013/0303884 A1* | 11/2013 | Kuntz | A61B 5/055 600/417 |
| 2015/0029178 A1* | 1/2015 | Claus | A61B 6/032 345/419 |
| 2020/0410666 A1* | 12/2020 | Wagner | G06N 3/08 |

FOREIGN PATENT DOCUMENTS

| | | |
|---|---|---|
| DE | 10 2008 054 298 A1 | 5/2010 |
| EP | 2656314 B1 | 2/2017 |

* cited by examiner

*Primary Examiner* — Amelie R Davis
(74) *Attorney, Agent, or Firm* — Knobbe, Martens, Olson & Bear LLP

(57) ABSTRACT

Methods for operating a medical imaging device for positionally correct representation of non-anatomical structures during an imaging examination may include providing a first 3D image containing at least one anatomical structure, extracting at least one anatomical model from the at least one anatomical structure, providing 2D update images recorded at different times, extracting non-anatomical and anatomical structures from subsets of the update images, calculating a non-anatomical 3D image from at least two partial reconstructions based on the extracted non-anatomical structures, reconstructing an anatomical 3D image based on the extracted anatomical structures, registering the anatomical 3D image with the first 3D image by determining a coordinate transformation, and creating a navigation volume from the anatomical model and the non-anatomical 3D image using the coordinate transformation.

15 Claims, 4 Drawing Sheets

(58) Field of Classification Search
CPC ......... A61B 6/466; A61B 6/486; A61B 90/36; A61B 6/4441; A61B 6/487; A61B 6/48
See application file for complete search history.

METHOD AND DEVICE FOR OPERATING A MEDICAL IMAGING DEVICE FOR THE POSITIONALLY CORRECT REPRESENTATION OF NON-ANATOMICAL STRUCTURES DURING AN IMAGING EXAMINATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to the field of medical imaging devices and methods, and more specifically to positionally correct representation of non-anatomical structures during an imaging examination.

Description of the Related Art

Projective medical imaging methods are often used in medical surgical interventions, such as 2D methods (e.g., methods which project the three-dimensional structure of a volume to be imaged onto a two-dimensional surface and thus generate 2D images). However, existing medical imaging methods have a number of disadvantages. 2D X-ray fluoroscopy may be used, in which 2D images such as 2D X-ray images are recorded in a chronological sequence and displayed on a display device. The information about the spatial (3D) nature of the patient and, for example, of the intervention material, that is to say its three-dimensional shape, is largely lost in this case, since all the structures which lie on a projection beam, for example an X-ray beam, are projected onto one point on a surface (e.g., these structures appear superimposed on a 2D image). 2D images consist of pixels to which different values, for example integer values such as 1 or 0, can be assigned. Thus, a structure lying on a projection beam, for example an X-ray beam, is projected onto a pixel of a 2D image, the values of pixels being dependent on the type and nature of the structures to be projected. If the attending physician were to have a chronologically rapid sequence of 3D reconstructions showing the introduced, non-anatomical structures, for example intervention materials, and the patient anatomy in a 3D view, he would receive a 4D view, e.g., three spatial dimensions plus one temporal dimension.

This means that the attending physician would be provided with a 4D interventional guidance for performing the intervention, which makes it possible to assess the position of the interventional material introduced into the patient at a current time.

For the provision of a 3D reconstruction, it may be necessary to record or produce a tomography which is carried out, for example, by means of computed tomography (CT), a C-arm X-ray apparatus (wherein the C-arm X-ray apparatus can be a mobile or stationarily installed C-arm X-ray apparatus), or by means of magnetic resonance tomography. A 3D reconstruction is a 3D volume calculated from a plurality of individual measurements. In computed tomography, the individual measurements are 2D X-ray projections. The continuous sequential execution of many 3D X-ray exposures, which may be necessary for a corresponding continuous recording of the patient and of the intervention material, is associated with a very high radiation exposure for the patient. This currently makes it difficult or impossible to use 4D interventional guidance in surgery, especially in vascular surgery. A computer tomography system can be any imaging device that records 2D projection images and uses them to calculate a tomographic image.

Existing methods for guiding intervention materials, in particular in blood vessels, comprises a great number of methods, and in particular X-ray-based imaging methods face the problem that blood vessels have virtually the same contrast as the surrounding tissue and are therefore initially not visible, in particular on X-ray images or computer tomography images. When recording X-ray images or computer tomography images, it may therefore be necessary to add a contrast agent to the vascular system, for example iodine or carbon dioxide, which has a higher or lower X-ray absorption than the surrounding tissue and thus makes the vascular system visible. When contrast medium is administered to the patient, a further effect can be that vessels of the vascular system which have no or only a reduced blood supply can also be noticed by the treating surgeon.

Images enhanced by using contrast media may be used in a variety of methods. In subtraction-based 2D imaging methods, such images can be used, after subtraction of an image (mask) without a contrast agent, for representing the dynamics of the blood flow or the shape of a vascular system in digital subtraction angiography (DSA) for example. They can also be used to insert a track for guiding an instrument in a vessel or a vascular system. In this case, however, contrast medium must again be administered, accompanied by an increased radiation load, with each change in the exposure geometry or movement of the patient. The repeated addition of iodine-containing contrast agents can also have a toxic effect on the kidneys in certain cases and thus be contraindicated in case of renal insufficiency. In addition, the depth information in the form of the third dimension is lost in the manner described in the preceding section.

It is therefore advisable to use a 3D reconstruction of the vessels, which can be extracted, for example, from a previously acquired contrast agent-filled computed tomography and superimposed on a live 2D image as a contour in the respectively correct position while determining and using the correct projection geometry.

The existing methods described above have a disadvantage in that the contrast medium-filled vessels and, if present, the non-anatomical structures can only be recognized by the treating physician on a live 2D image. Even if multiple X-ray apparatuses are used, especially C-arm X-ray apparatuses, more particularly mobile C-arm X-ray apparatuses, which can have different projection directions, such as orthogonal projection directions, complete 3D information is not available A considerable amount of time, radiation dose and contrast medium for example, which represents an enormous burden for the patient to be treated, may therefore be required in order to correctly navigate a guide wire within a vascular system.

Document EP2656314B1 discloses a method and a system which, based on a compressed scan, permit radiological guidance of an instrument during a medical examination.

Existing techniques have the additional disadvantage that the 2D X-ray projections required for the 3D reconstructions of the intervention materials at a certain point in time must be recorded simultaneously or almost simultaneously (pseudo-simultaneously) in order to reproduce the intervention materials correctly in the presence of movements, in particular those caused by the guidance of an instrument by the treating physician. On the other hand, if there is a time offset between the recordings of individual or multiple 2D X-ray projections, a consistent 3-D reconstruction at a given point in time is generally not possible. Depending on the amount of movement that occurs, movement artifacts can occur here, or the 3D reconstructions can become completely unsuitable. Such a time offset arises especially if the X-ray apparatus used for the exposure has too few image chains (e.g., X-ray source/detector pairs), since in this case the X-ray system has to change the exposure geometry between the exposure of 2D update projections, for example by rotation of a gantry. If this rotation is not fast enough, the above-described disadvantage of inconsistent and possibly unusable 3D reconstruction arises.

One solution to this problem is to enable a very rapid change in the recording geometry, for example by means of a rapidly rotating gantry. However, this places high demands both on the mechanical mounting of the X-ray system, for example a gantry, and on the parts installed therein, as well as on the components required for recording 2D X-ray projections. Specifically, in order to maintain low motion blur in the recorded 2D X-ray projections, which is produced by the rapid change in the recording geometry during the exposure of the X-ray detectors, the X-ray source must radiate in very short, but comparatively intensive pulses, and/or the recording rate of the X-ray detectors must be very high. This generally increases the cost of such a system or is not technically possible if X-ray flat-panel detectors are used. Accordingly, improved methods may be desirable.

SUMMARY

An example problem addressed by certain embodiments of the present technology is that of representing non-anatomical structures during an imaging examination in a positionally correct manner. Without limiting the scope of the present disclosure, certain advantageous features are recited in the claims of the present application.

In a first aspect, a method for operating a medical imaging device for the positionally correct representation of non-anatomical structures during an imaging examination comprises providing a first 3D image which contains at least one anatomical structure; extracting at least one anatomical model from the at least one anatomical structure of the first 3D image; providing at least two 2D update images captured at different times; extracting non-anatomical structures from a first subset of the 2D update images; extracting anatomical structures from a second subset of the 2D update images; calculating a non-anatomical 3D image from at least two partial reconstructions, wherein the at least two partial reconstructions are calculated from the extraction of the non-anatomical structures; reconstructing an anatomical 3D image from the extraction of the anatomical structures; registering the anatomical 3D image with the first 3D image by determining a coordinate transformation; and creating a navigation volume based on the at least one anatomical model and the non-anatomical 3D image by using the determined coordinate transformation.

In some embodiments, the navigation volume is additionally created based on the anatomical 3D image by using the determined coordinate transformation.

In some embodiments, providing the first 3D image comprises receiving the first 3D image from an X-ray C-arm apparatus, a computer tomography system, or a magnetic resonance tomography system.

In some embodiments, providing the 2D update images comprises receiving the 2D update images from an X-ray C-arm apparatus or a computer tomography system.

In some embodiments, in the absence of non-anatomical structures in a 2D update image of the first subset, the non-anatomical 3D image is further reconstructed.

In some embodiments, newly acquired 2D update images are added to at least one of the first subset and the second subset, and wherein at least one of the non-anatomical 3D images and the anatomical 3D images are reconstructed at a temporal rate corresponding to a function of an acquisition rate of the 2D update images.

In some embodiments, the method further comprises, when a new 2D update image has been acquired, adding the new 2D update image to the second subset of the provided 2D update images; and at least partially reconstructing the anatomical 3D image again in a further reconstruction, wherein all temporally older 2D update images are reused or removed for the further reconstruction.

In some embodiments, the calculation of the non-anatomical 3D image from the at least two partial reconstructions is performed by using a machine learning method comprising a neural network.

In some embodiments, movements of a patient that occur are taken into consideration.

In some embodiments, the extraction of the anatomical and non-anatomical structures from the 2D update images is performed using at least one machine learning method comprising a neural network.

In some embodiments, the non-anatomical 3D image is calculated based at least in part on the 2D update images by using a single machine learning method comprising a neural network.

In some embodiments, only those non-anatomical structures that belong to a predetermined object class or combination of object classes are extracted.

In some embodiments, non-anatomical structures that belong to a predetermined object class or combination of object classes are reconstructed separately.

In some embodiments, the non-anatomical structures comprise at least one of a guide wire and a catheter.

In a second aspect, a medical imaging device, in particular a gantry-based system, for carrying out an imaging examination and representation of non-anatomical structures, comprises a provisioning unit configured to provide a first 3D image, the first 3D image including at least one anatomical structure; at least two image chains configured to record at least one of 2D update images and 3D images; a computing unit comprising one or more processors; and a display. The one or more processors are configured by computer-executable instructions stored in the computing unit to at least extract an anatomical model from the at least one anatomical structure in the first 3D image; extract anatomical and non-anatomical structures from the 2D update images; calculate partial reconstructions from the extraction of non-anatomical structures; calculate a non-anatomical 3D image from at least two of the partial reconstructions; calculate an anatomical 3D image from the extraction of anatomical structures; and create a navigation volume from the anatomical model and the non-anatomical 3D image by determining a coordinate transformation, wherein the coordinate transformation causes the anatomical model to be positioned correctly in the navigation volume. The display is configured to display the navigation volume.

DETAILED DESCRIPTION

Figure 1:
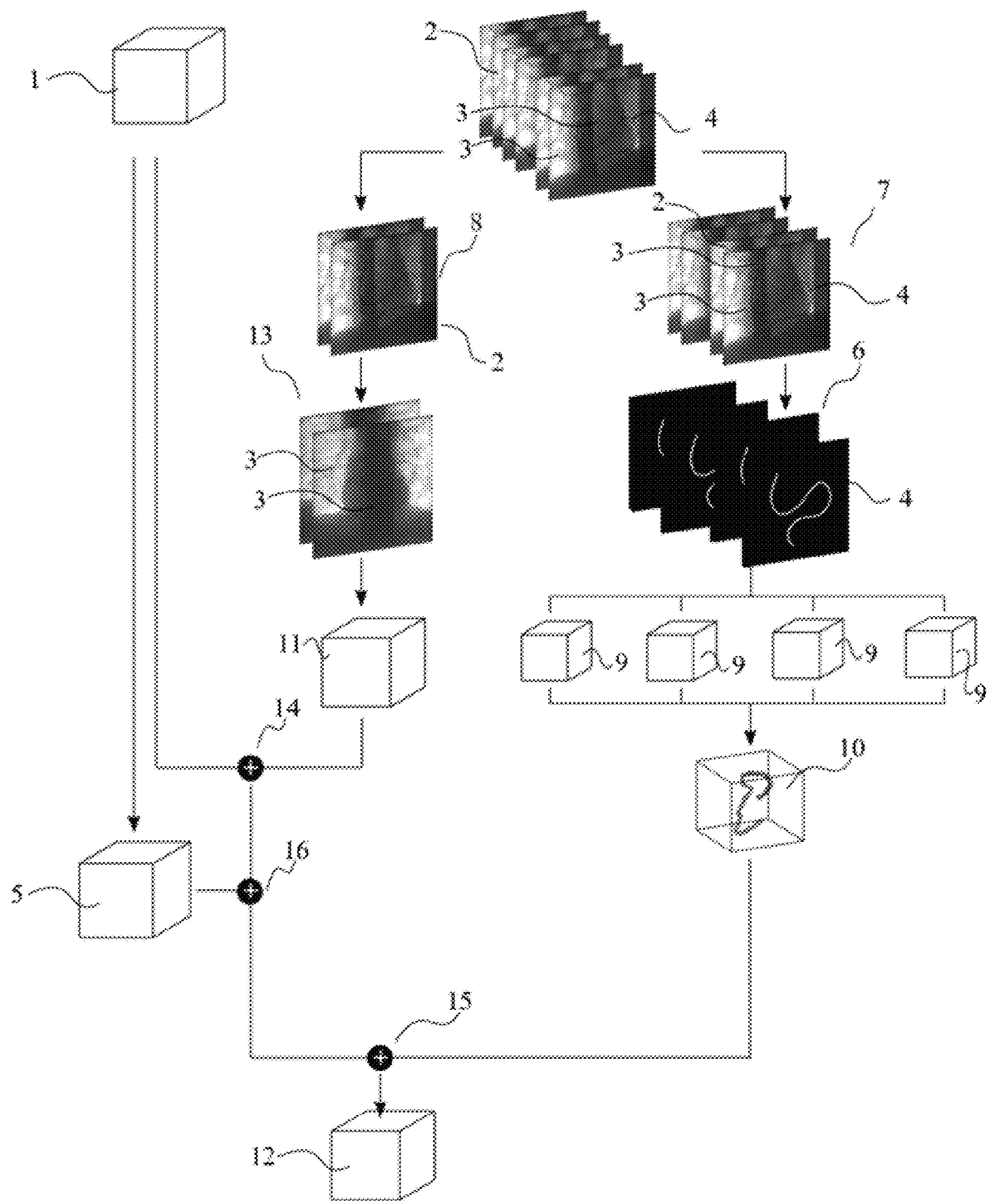
FIG. 1 schematically shows a sequence of an example method according to the present disclosure.

The present disclosure relates to a method for operating a medical imaging device for the positionally correct representation of non-anatomical structures during an imaging examination. The present disclosure further relates to medical imaging devices.

In medical surgical interventions, for example in vascular surgery, an aim is to carry out these interventions in a minimally invasive manner in the interior of the body of a patient to be treated, since such a minimally invasive procedure represents as little stress as possible for the patient to be treated. The interior of the body may be accessed via small incisions made by the attending physician or, alternatively, via body openings of the patient. Because the target area of such a procedure is difficult to see or not externally visible to the treating physician in a great many procedures, non-anatomical structures, in particular intervention materials, for example guide wires, catheters, stents, coils, screws, (e.g., structures which are introduced into the patient for the procedure), and the surrounding patient anatomy (anatomical structures) are visualized by imaging methods.

Embodiments of the present disclosure provide a number of advantages including addressing the problem of providing an improved method for positionally correct representation of non-anatomical structures and anatomical structures during an imaging examination.

In some embodiments of the present technology, this problem may solved by implementing a method for operating a medical imaging device for the positionally correct representation of non-anatomical structures during an imaging examination. Example methods of the present disclosure can include providing a first 3D image which contains at least one anatomical structure; extracting at least one anatomical model from the at least one anatomical structure of the first 3D image; providing at least two 2D update images, wherein at least two 2D update images have been recorded at different times; extracting non-anatomical structures from a first subset of the 2D update images; extracting anatomical structures from a second subset of the 2D update images; calculating a non-anatomical 3D image from at least two partial reconstructions, wherein the at least two partial reconstructions are calculated from the extraction of the non-anatomical structures; reconstructing an anatomical 3D image from the extraction of the anatomical structures; registering the anatomical 3D image with the first 3D image, by determining a coordinate transformation; and creating a navigation volume from the at least one anatomical model and the non-anatomical 3D image by using the determined coordinate transformation.

Methods and devices according to the present technology may take advantage of the provision of a first 3D image (3D volume). The first 3D image can be recorded either during an interventional procedure by means of a 3D recording or, for example, loaded from a patient archive, the first 3D scan having been recorded preoperatively if the first 3D image is loaded from a patient archive. The first 3D image, which contains at least one anatomical structure, can be prepared, for example, by a pre-operative computed tomography or magnetic resonance tomography recording. The at least one anatomical structure of the first 3D image can include, in part, bone and/or in part vascular structures as well as surrounding anatomy, for example organs, muscles or other soft tissues. In addition, the first 3D image may have further non-anatomical structures, for example implants or intervention materials from previous surgical procedures, and further anatomical structures, for example skin edges. Alternatively, the first 3D image can also be recorded intra-operatively, preferably using an intra-operative computed tomography system or a C-arm X-ray apparatus, such as a mobile C-arm X-ray apparatus or the like.

The first 3D image can be recorded by means of the apparatus which is subsequently used for 4D intervention guidance. It is also possible to import the first 3D image into an internal storage unit, for example an internal image data memory, or an external storage unit, for example a USB stick, an external hard disk, or an online memory to which the imaging apparatus implementing the method according to the invention, preferably an X-ray machine, has access. An anatomical model of the at least one anatomical structure of the first 3D image can be extracted prior to or following the import.

In accordance with the present disclosure, an extraction can be a calculation of an anatomical model, wherein the model can correspond, for example, to a voxel-based segmentation or to a parametric representation. For instance, if the at least one anatomical structure is in particular an organ, preferably a hollow organ such as a contrast medium-containing blood vessel or a contrast medium-containing heart chamber or an intestine, then a model of the surface of the hollow organ may be calculated. If the at least one anatomical structure is, for example, a bone such as a vertebral body, then, for example, a segmentation of all the associated voxels of the anatomical structure can be calculated.

The present disclosure further provides that at least two 2D update images can be subsequently made available, the 2D update images containing at least in part anatomical structures and/or at least in part non-anatomical structures of an examination zone. The at least partial anatomical structures can be parts of the bone structures or parts of the vascular structures or parts of bone and vascular structures. The non-anatomical structures may be intervention materials introduced into the patient to be treated, such as guide wires, catheters, stents, coils or screws. The at least two 2D update images made available can be newly recorded 2D update images in part and in part 2D update images that were recorded during the surgical procedure and were used to calculate a 3D reconstruction. The at least two 2D update images may have been recorded by means of an X-ray apparatus, for example a C-arm X-ray apparatus or a computer tomography system (gantry-based system), the non-anatomical structures and/or the anatomical structures having possibly undergone a change of position during the surgical procedure, and the non-anatomical structures having possibly been moved, for example, by a movement within the patient or by the advancement of a guide wire. The anatomical structures may have experienced, for example, a change in position due to the patient's breathing or due to displacement of the patient by the treating surgeon. The 2D update images provided, such as the 2D update images newly provided (e.g., last recorded), may be 2D update images recorded in a time interval. For example, the 2D update images may include at least two 2D update images recorded almost simultaneously ("pseudo-simultaneously") or simultaneously at one point in time. In variants of the method in which 2D update images are not recorded simultaneously, the 2D update images can be recorded, for example, with a single recording device such as a single image chain. In accordance with the present disclosure, at least two of the provided 2D update images can be recorded at different times with different viewing directions, since the number of 2D update images used for calculating a 3D reconstruction of the non-anatomical structures may generally exceed the number of available image chains.

The provision of the at least two 2D update images can be followed by an extraction of non-anatomical structures from a first subset of the at least two 2D update images, wherein the first subset of the at least two 2D update images can include, for example, zero, one, two, three, or more 2D update images. The first subset can be different from potential further subsets in that they can differ completely or partially. For example, the subsets may contain entirely different subsets of images or may share some images in common, the number of 2D update images in the two subsets possibly being different. The extraction can correspond, for example, to a discrete, pixel-by-pixel segmentation. In an advantageous embodiment of the present disclosure, the extraction can also represent continuous values, in particular contributions of the non-anatomical structures to the 2D update images and here in particular physically correct or approximately correct line integrals along the projection beams.

Anatomical structures can additionally be extracted from a second subset of the 2D update images. This extraction of anatomical structures can also take place in a manner in which the extracted non-anatomical structures are removed from the 2D update images according to their contribution thereto, e.g., by subtraction. An advantageous configuration provides that the anatomical structures can be extracted in such a manner that no visible or measurable gaps, corresponding to air for example, occur in the resulting images at the positions of non-anatomical structures, but rather the extraction is carried out in such a manner that the result corresponds to the case that would exist if no non-anatomical structures were present at the corresponding points, and the corresponding pixels were occupied by the tissue that surrounds the corresponding positions.

Following the extraction of the non-anatomical structures from the first subset of the 2D update images, a non-anatomical 3D image can be calculated from at least two partial reconstructions, the at least two partial reconstructions being calculated from the extractions. Due to the limited number of possible recording devices, the quantity of 2D update images that can be provided may contain an inadequate number of 2D update images that were recorded simultaneously or pseudo-simultaneously. In order to reconstruct a non-anatomical 3D image from the set of 2D update images recorded simultaneously or pseudo-simultaneously after the extraction has taken place, the first subset can contain 2D update images which were recorded at different times. Consequently, the extractions also represent different points in time and can thus represent different states of the non-anatomical structures, in particular different positions and orientations, due to possible movement of the patient and/or the non-anatomical structures. In order to take into account that the extractions can display different states of the non-anatomical structures, only those extractions which were recorded simultaneously or pseudo-simultaneously can be initially recalculated back into a common 3D volume, referred to herein as a partial reconstruction (e.g., using a projection geometry under which the 2D update images were recorded). These images recorded simultaneously or pseudo-simultaneously can originate from different recording devices present in the system, in particular image chains, for example X-ray source/detector pairs. Thus, each partial reconstruction can be consistent in itself and with respect to the represented state of the non-anatomical structures.

However, in general, neither individual partial reconstructions nor the combination thereof can be understood as a suitable non-anatomical 3D image, since the partial reconstructions contain artifacts which are caused by the fact that the number of the extractions on which each partial reconstruction is based is small; for example, a filtered or unfiltered rear projection can be used to calculate the partial reconstructions. The combination of several partial reconstructions according to conventional methods known in computed tomography thus may not not yet permit a correct representation of the non-anatomical structures. However, it is possible to combine the partial reconstructions by means of those image processing operations that have the purpose of removing these artifacts. In order to keep the computation time for such a method as short as possible, computation operations can preferably be used which utilize the fact that both the partial reconstructions and the non-anatomical 3D image are typically largely empty because only a small part of the examination zone typically contains non-anatomical structures. For the removal of the artifacts of the partial reconstructions, it thus is possible to use machine learning methods which, by means of a plurality of uncorrected input images such as a number of partial reconstructions, learn to reconstruct corrected output images, in particular correct non-anatomical 3D images, which now do not contain any artifacts associated with an insufficient number of 2D update images. Machine learning methods can be particularly successful here because the non-anatomical structures generally have a high symmetry, for example cylindrical in the case of a guide wire, which makes it possible to learn their actual shape.

A reconstruction of an anatomical 3D image from the anatomical structures extracted from the second subset of the 2D update images can be carried out serially or in parallel with the calculation of the non-anatomical 3D image. The anatomical 3D image may show only the patient anatomy, but not the non-anatomical structures. This anatomical 3D image can contain structures whose motion is generally significantly smaller in speed and/or amplitude than the structures contained in the non-anatomical 3D image, which are usually actively guided. However, since the patient anatomy contained therein is best converted into a 3D image from a comparatively large number of 2D update images, it is possible to calculate the 3D images from a comparatively large number of 2D update images taken over a relatively long period of time.

The inventors recognized that a 3D real-time display of intervention materials in a patient anatomy may require only the 3D real-time reconstructions of the intervention materials from a few projections, while the 3D reconstruction of the patient anatomy requires many 2D update images, which can, however, be recorded over a longer period of time. The inventors additionally recognized that the described separation of the corresponding 3D reconstructions permits dose-reduced imaging, particularly if the 2D update images are 2D X-ray projections, since the 2D X-ray projections can be recorded at a comparatively low time rate, for example 5 per second or 10 per second.

After the reconstruction of the anatomical 3D image, the anatomical 3D image can be registered with the first 3D image by determining a coordinate transformation. For example, the anatomical 3D image can be transferred into the coordinate system of the first 3D image or the first 3D image can be transferred into the coordinate system of the anatomical 3D image. An advantage of such a procedure can be that it is possible to detect changes which have occurred between the anatomical 3D image and the first 3D image, which contains the at least one anatomical structure, such as a vessel made visible by contrast media. These changes can be caused in particular by the fact that the first 3D image can be acquired with an imaging device other than that used for acquiring the 2D update images. Since differences between the anatomical 3D image and the non-anatomical 3D image are generally comparatively small and are essentially limited to the movements of the non-anatomical structures such as a guide wire or a catheter, the specific coordinate transformation now also applies between the first 3D image and the non-anatomical 3D image. It is thus possible to display the non-anatomical 3D image, for example a guide wire or a catheter within a vessel, in the correct position with respect to the first 3D image, and thus with respect to the at least one anatomical structure. This anatomical structure is only visible in the first 3D image, for example by the single use of a contrast agent within a blood vessel, but not in the anatomical 3D image, which generally does not show the anatomical structure, since, for example, a contrast agent cannot be administered continuously.

After registration, a navigation volume can thus be produced from the at least one anatomical model, the non-anatomical 3D image and, in alternative embodiments of the present disclosure, additionally the anatomical 3D image, using the determined coordinate transformation. Thus, both the non-anatomical structures from the non-anatomical 3D image, the extracted anatomical model and, in alternative embodiments of the method according to the invention, the anatomical structures from the anatomical 3D image are additionally represented in the correct position relative to one another in the navigation volume. The coordinate transformation which was determined from the anatomical 3D image and the first 3D image may be deformable. When determining the coordinate transformation, the contrast agent-containing regions of the first 3D image may not be taken into account, if present, since they can falsify the determination of the coordinate transformation. The determination of the optionally deformable coordinate transformation between the first 3D image and the anatomical 3D image can be understood as image registration.

In some embodiments, the first subset of the 2D update images, from which the non-anatomical 3D image is calculated, can be the most recently recorded 2D update images, for example the last two or three 2D update images, it being possible for the number of 2D update images of the first subset to be set by a user in an organ program of the medical imaging device. This organ program can also be set such that, for example, any number up to all recorded 2D update images are used for the reconstruction of the non-anatomical 3D image.

In some embodiments, if no non-anatomical structure is present in a 2D update image of the first subset, the non-anatomical 3D image can likewise be reconstructed according to the present disclosure, this non-anatomical 3D image being empty (e.g., containing only zeros).

Furthermore, in some embodiments, the non-anatomical 3D images and/or the anatomical 3D images can be reconstructed, in particular, at a time rate, the time rate of the reconstruction of the anatomical 3D images corresponding to the recording rate of the 2D update images. The reconstruction at a time rate makes it possible for the non-anatomical 3D image to be reconstructed, for example, in real time and displayed in the navigation volume. The reconstruction of the non-anatomical 3D images in real time can be achieved in particular because non-anatomical structures, in particular intervention materials, for example cylindrical structures such as guide wires, generally have a high symmetry, particularly along their axial axis, and because the non-anatomical structures preferably fill only a small proportion of the volume to be imaged, and therefore these non-anatomical structures can be reconstructed from only a few 2D update images.

In some embodiments, when a new 2D update image is recorded, it can be added to the second subset of the 2D update images provided, and the anatomical 3D image can be reconstructed at least partially, wherein older 2D update images can be re-used for the reconstruction. This may be referred to as an overlapping reconstruction. One possibility of keeping the computation outlay for the method according to the invention for this purpose low is that of adding only at least one newly acquired 2D update image to the anatomical 3D image during the reconstruction, for example by means of filtered back-projection, and removing the oldest 2D update image which falls out of a time window from the anatomical 3D image by subtraction, for example by subtraction of its filtered back-projection. The number of 2D update images in the second subset can be set by the user in an organ program. It is also possible to incorporate any available information about the movement of the patient, for example respiratory movement, cardiac movement, patient table movement, into the reconstruction of the anatomical 3D image.

In some embodiments, various portions of the disclosed methods can be accomplished by using a machine learning method such as a neural network (e.g., a convolutional neural network). For example, in some embodiments, a machine learning method can be used for extracting the at least one anatomical model from the at least one anatomical structure of the first 3D image. An advantage of these embodiments can be that only a few 2D update images, or even a single 2D update image, may be required in order to reconstruct a non-anatomical 3D image.

Generally, a machine learning method can be configured to transform input data into output data according to a specific transformation. In order to enable the machine learning method to carry out the desired transformation, its free parameters can be suitably set or learned in an iterative process (called training). This is preferably done in a monitored training in which a plurality of pairs (called training pairs) are presented to the machine learning method, each pair consisting of a possible input data item on the one hand and an output data item associated with the transformation to be learned on the other hand. In this case, the free parameters of the network are iteratively adapted in such a way that the value of a function, preferably a cost function, which measures the deviation between the actual output data and the desired output data in accordance with the transformation to be learned, is minimized. The training pairs may be created by realistic simulation because a large number of training pairs can be generated in this way. It can be advantageous in this regard that the accuracy of the machine learning method increases with the number of training pairs. In some embodiments, by means of realistic simulation of non-anatomical structures and realistic simulation of partial reconstructions obtained therefrom, which contain these non-anatomical structures, a large number of training pairs are generated, each training pair consisting of a set of partial reconstructions on the one hand and the associated non-anatomical 3D image on the other.

Some embodiments may take account of movements of the patient that may occur, for example breathing movement, heart movement or patient table movement, These movements can be taken into consideration implicitly, because the partial reconstructions represent separate input channels for the method according to the invention. The consideration can also be carried out explicitly in that the method can be preceded by such a method which initially carries out a movement correction separately. For example, translation, rotation and/or deformation can be corrected. The method can be a machine learning method for example, in particular a neural network such as a convolutional neural network.

In some embodiments, the extraction of the anatomical and non-anatomical structures from the 2D update images, can further be performed by at least one machine learning method, for example, a neural network such as a convolutional neural network. An advantage of these embodiments can be that machine learning methods can carry out transformations, which are similar to the extraction of a segmentation disclosed in the preceding section, with high accuracy.

In some embodiments, the calculation of the non-anatomical 3D image from the 2D update images can be carried out by a single machine learning method, for example by a neural network which was trained to first convert 2D update images into other 2D images, for example into extracted anatomical structures or non-anatomical structures, these other 2D images subsequently being reconstructed in the same machine learning method to form an artifact-free non-anatomical 3D image.

In some embodiments, the non-anatomical structures can be extracted in such a way that only specific non-anatomical structures are extracted, for example those which belong to a specific predetermined object class, or to a specific predetermined combination of a plurality of object classes. Subsequently only those non-anatomical structures that show these specific non-anatomical structures (e.g., those which belong to the specific object class, or to the specific combination of a plurality of object classes) can be reconstructed to form non-anatomical 3D images. If a machine learning method is used for the extraction, it can correspondingly be trained not only for the extraction but also for the differentiation of such non-anatomical structures. In such alternative embodiments, it may be advantageous to extract and reconstruct only this guide wire, for example, when navigating a guide wire in a patient. Further non-anatomical structures which are already present, for example, and in particular belong to other object classes, such as stents or orthopaedic implants from previous interventions, or non-intervention-specific non-anatomical structures, for example the patient table, which are then not of interest, can then be neither extracted nor reconstructed, so that the representation displayed to the attending physician is reduced to the essential.

In some embodiments, the non-anatomical structures can be extracted in such a way that a plurality of separate extractions are calculated from each 2D update image, each of the separate extractions showing only a subset of the non-anatomical structures, for example only those which belong to a specific object class, or to a specific combination of a plurality of object classes. The extractions can then be processed separately to form non-anatomical 3D images, the separate non-anatomical 3D images thus calculated containing only the corresponding subset of the non-anatomical structures. The separate non-anatomical 3D images can then be combined to form a single non-anatomical 3D image, for example by the addition of voxel-based separate non-anatomical 3D images. It can be advantageous in such embodiments that a 3D anatomical image generated by separate 3D reconstructions of subsets of the non-anatomical structures and subsequent combination can be more accurate than a 3D anatomical image reconstructed all at once, because the reconstruction problem is generally simpler if the proportion of the non-anatomical structures in the volume to be imaged is smaller.

Another aspect of the present disclosure relates to a medical imaging device, particularly a gantry-based system, for performing an imaging examination and representation of non-anatomical structures. The medical imaging device can include a provisioning unit for providing a first 3D image, the first 3D image including at least one anatomical structure; at least two image chains, wherein the image chains are designed for recording 2D images, in particular 2D update images and/or 3D images; a computing unit; and a display unit. The computing unit can be configured to extract an anatomical model from the at least one anatomical structure, extract anatomical and non-anatomical structures from the 2D update images, calculate partial reconstructions from the extraction of non-anatomical structures, calculate a non-anatomical 3D image from at least two partial reconstructions, calculate a 3D anatomical image from the extraction of anatomical structures, and create a navigation volume from the anatomical model and the non-anatomical 3D image by determining a coordinate transformation, wherein the coordinate transformation is configured to position the anatomical model correctly in the navigation volume. The navigation volume can be displayed on the display unit.

The medical imaging devices of the present disclosure may contain a provisioning unit, which may include, for example, a memory unit such as a memory stick, a hard disk or another portable or permanently installed data carrier. The provisioning unit can also be understood as a connection to a memory unit that is connected to a network to which the medical imaging device has access, in order thus to provide a first 3D image, the first 3D image containing at least one anatomical structure.

The medical imaging devices of the present disclosure may also contain at least two image chains, and the device according to the invention can also comprise, for example, three, four or more image chains. In this context, an image chain may include an X-ray generator for generating X-rays, for example a rotating anode-based generator, and a receiver unit for receiving X-rays, for example a flat-panel detector, the image chains being designed to receive 2D images, in particular 2D update images, and/or 3D images.

When at least two image chains are used, it can be advantageous that a plurality of 2D update images can be recorded simultaneously, pseudo-simultaneously or directly in succession. The medical imaging device preferably contains two image chains, since a higher number of image chains increases the complexity, the cost and the failure probability of the medical imaging device. 2D update images are preferably recorded in tuples, the gantry-based system preferably not having rotated or approximately not having rotated further between the recording of 2D update images of a tuple. On the other hand, the gantry-based system can preferably rotate further through a minimum angle of, for example, at least 5° or 20° between recording tuples. The rotational speed of the gantry-based system is preferably low, because motion blur can occur if the rotational speed is too high.

Furthermore, the medical imaging devices according to the present disclosure can contain a computing unit; this computing unit can include one or more processors such as a graphics processing unit (GPU) or some other processor unit, for example a central processing unit (CPU), and if this computing unit is a GPU, it can be used for carrying out massive or highly parallel computing operations. A computing unit can also include a plurality of computing units (e.g., including a plurality of processors), which in their entirety can again be regarded as a computing unit according to the present disclosure. Furthermore, this computing unit can extract an anatomical model from the anatomical structure of the first 3D image. The computing unit may also be designed to extract anatomical and non-anatomical structures from the at least two 2D update images. Furthermore, the computing unit can reconstruct at least two partial reconstructions from the extractions of the non-anatomical structures of the first subset of the 2D update images and likewise can reconstruct an anatomical 3D image from the extraction of anatomical structures of the second subset of 2D update images. The computing unit may also be designed for calculating a non-anatomical 3D image from at least two partial reconstructions. The computing unit may additionally be configured to create a navigation volume from the anatomical model, the non-anatomical 3D image and optionally from the anatomical 3D image by determining a coordinate transformation, wherein the coordinate transformation is configured to position the anatomical model, the non-anatomical 3D image and optionally the anatomical 3D image correctly in the navigation volume.

Furthermore, the medical imaging devices of the present technology can contain a display unit on which the navigation volume is displayed, as well as optionally the non-anatomical 3D image, the anatomical 3D image, the first 3D image and/or the anatomical model. The display unit can also be configured to display the 2D update images. In further advantageous embodiments of the present disclosure, and in particular when the gantry is at a standstill, the display unit can additionally display conventional X-ray images, for example fluoroscopies, and X-ray images post-processed by the computing unit, by means of a frequency filter for example. In some embodiments, the display unit can display images that have been calculated by means of a subtraction method on the computing unit, for example a digital subtraction angiography (DSA) image. The display unit can include any suitable display device capable of displaying images and/or video.

Referring now to the figures, FIG. 1 shows an example sequence of a method according to the present disclosure. First, a first 3D image 1 (3D volume) is provided. This first 3D image 1 can be captured during or before an interventional procedure by means of a 3D recording. An anatomical model 5 is further extracted from this first 3D image 1.

At least two 2D update images 2 are subsequently provided, the 2D update images 2 containing at least in part anatomical structures 3 and/or at least in part non-anatomical structures 4 of an examination zone. The at least partial anatomical structures 3 are parts of the bone structures and/or parts of the vascular structures and/or parts of the soft tissue. A guide wire is present as a non-anatomical structure 4 in an examination region in FIG. 1. Furthermore, the at least two 2D update images 2 may have been recorded in a time interval.

Following the provision of the at least two 2D update images 2, an extraction 6 of non-anatomical structures 4 from a first subset 7 of the at least two 2D update images 2 is carried out.

Based on these extractions 6 of the non-anatomical structures 4 from the first subset 7 of the 2D update images 2, a calculation of a 3D non-anatomical image 10 from multiple partial reconstructions 9 is performed. In FIG. 1, this is done from four partial reconstructions 9. The various partial reconstructions 9 preferably originate from 2D update images which were acquired at different points in time and can thus, due to possible movements of the patient and/or the non-anatomical structures, represent different states, positions and orientations of the non-anatomical structures 4.

In addition to the extraction 6 of the non-anatomical structures 4, an extraction 13 of the anatomical structures 3 from a second subset 8 of the 2D update images 2 is also performed, wherein the second subset 8 differs from the first subset 7 in at least one 2D update image 2, so that the two subsets 7, 8 are not identical. A 3D anatomical image 11 is calculated from the extraction 13 of anatomical structures 3.

After the reconstruction of the anatomical 3D image 11, a registration of the anatomical 3D image 11 with the first 3D image 1 can be carried out by determining a coordinate transformation 14. Then there is an application 16 of the coordinate transformation 14 thus obtained to the anatomical model 5. The coordinate transformation determined from the anatomical 3D image 11 and the first 3D image 1 can be deformable. When determining the coordinate transformation 14, the contrast agent-containing regions of the first 3D image 1, if present, may advantageously be considered, since they can falsify the determination of the coordinate transformation.

Finally, a navigation volume 12 can be created 15 from the at least one anatomical model 5 and the non-anatomical 3D image 10. Thus, not only the non-anatomical structures 4 from the non-anatomical 3D image 10, but also the extracted anatomical model 5 are displayed in the correct position relative to one another in the navigation volume 12.

Figure 2:
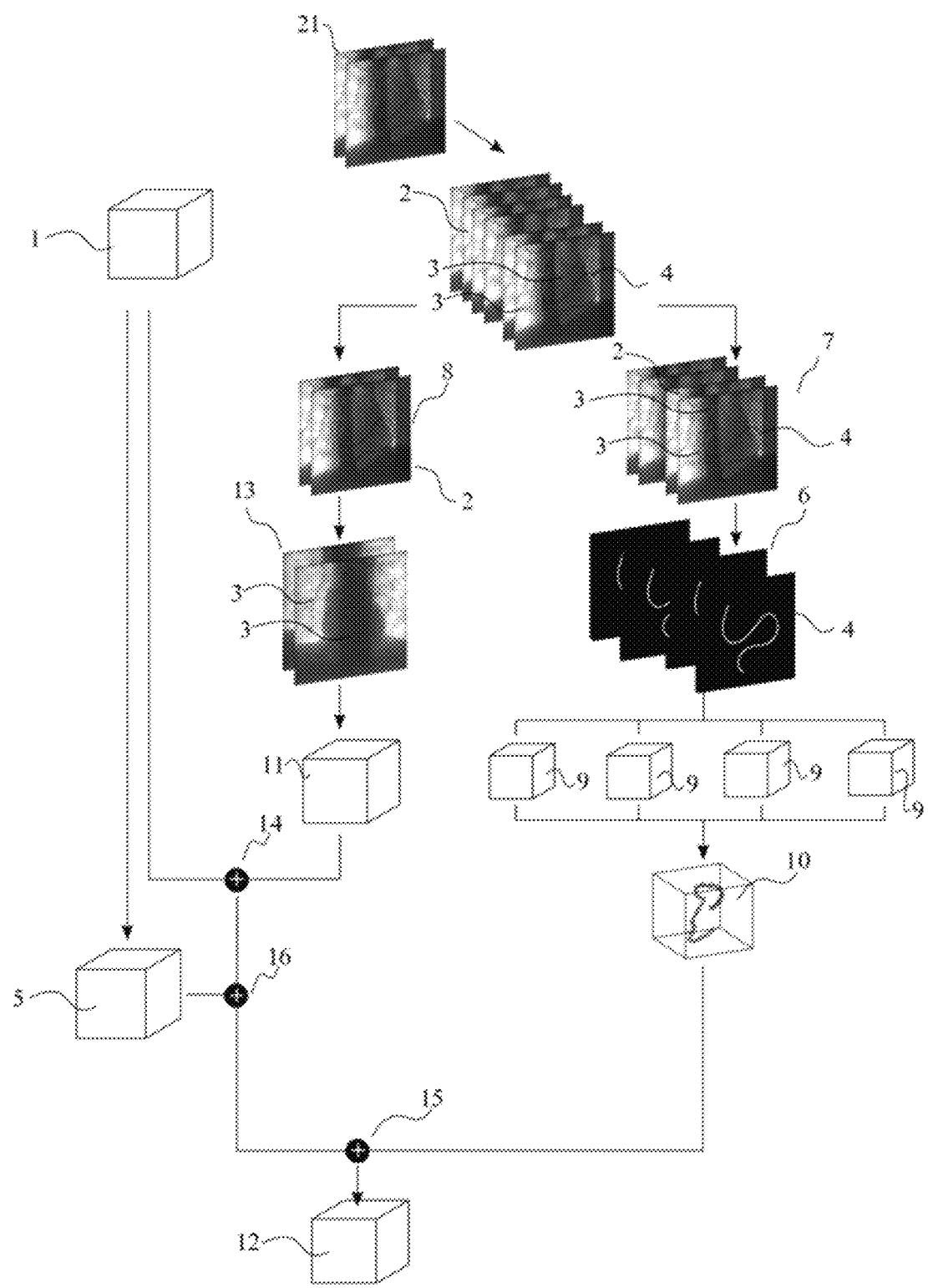
FIG. 2 schematically shows a sequence of an example method according to the present disclosure, in which new 2D update images are added.

FIG. 2 shows a sequence of an example method according to the present disclosure in which, after acquisition of two new 2D update images 21, the two new 2D update images 21 are added to the first subset 7 and to the second subset 8 of the provided 2D update images 2, and the anatomical 3D image 11 is at least partially reconstructed once again, whereby all temporally older 2D update images 2 can be reused for the new reconstruction of the anatomical 3D image 11. Furthermore, the non-anatomical 3D image 10 can be reconstructed by means of the new 2D update images 21. The example method illustrated in FIG. 2 may be especially advantageous at the beginning of the imaging, for example, when there are not yet sufficient 2D update images 2 in the second subset 8 in order to reconstruct from them an anatomical 3D image 11 with low artifacts. By increasing the number of 2D update images 2 in the second subset 8, a higher image quality can be achieved.

Figure 3:
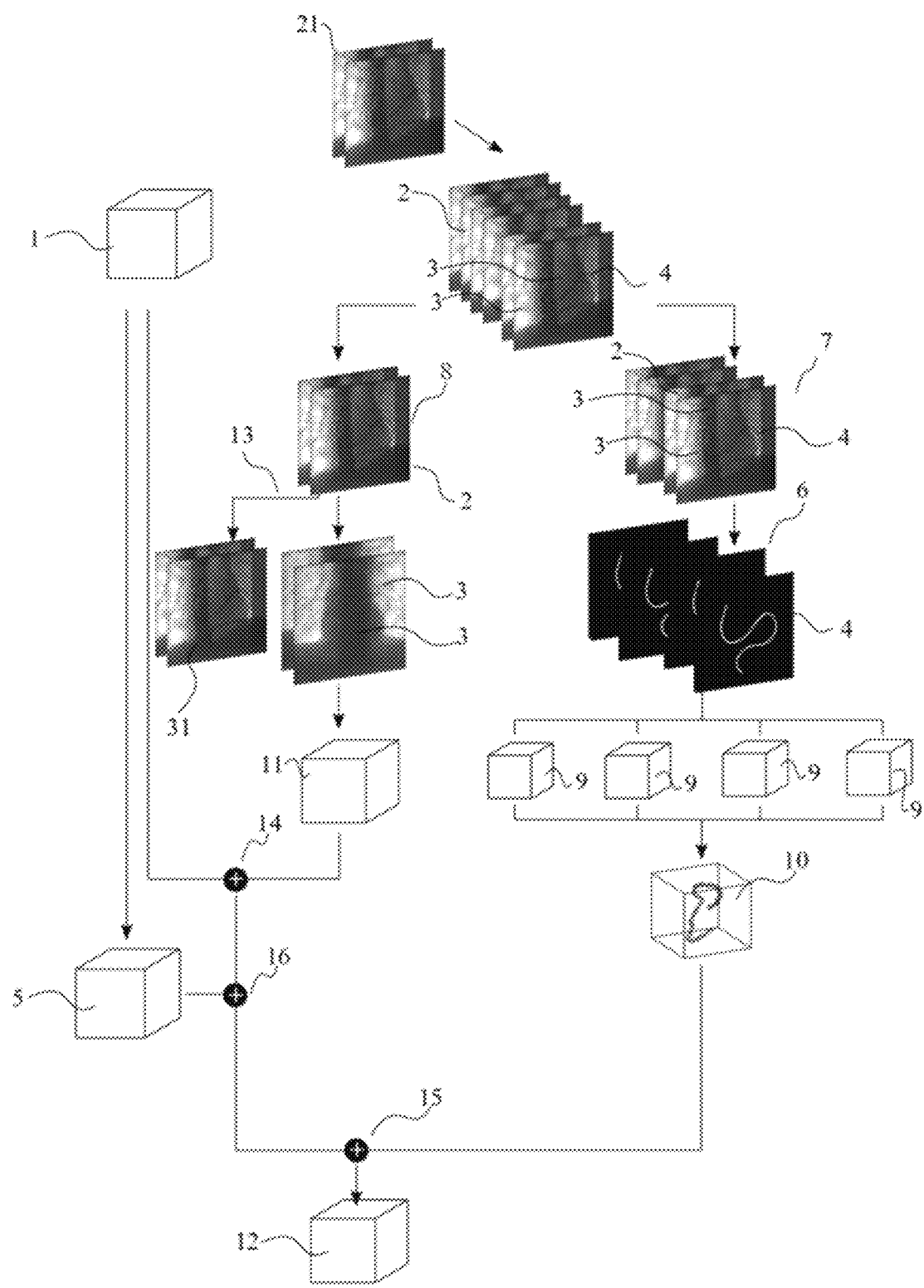
FIG. 3 schematically shows a sequence of an example method according to the present disclosure, in which new 2D update images are added and old 2D update images are replaced thereby.

FIG. 3 shows an embodiment of an example method in which two newly recorded 2D update images 21 are added to the second subset 8 and the oldest two 2D update images 31 are removed from the second subset. A 3D anatomical image 11 is then calculated from the second subset modified in this way. This may be referred to as an overlapping reconstruction. It may be advantageous in this embodiment that the anatomical 3D image modified in this way now contains more up-to-date information about the anatomical structures 3, which may have changed, for example, due to respiratory motion, cardiac motion or movement of the patient table.

Figure 4:
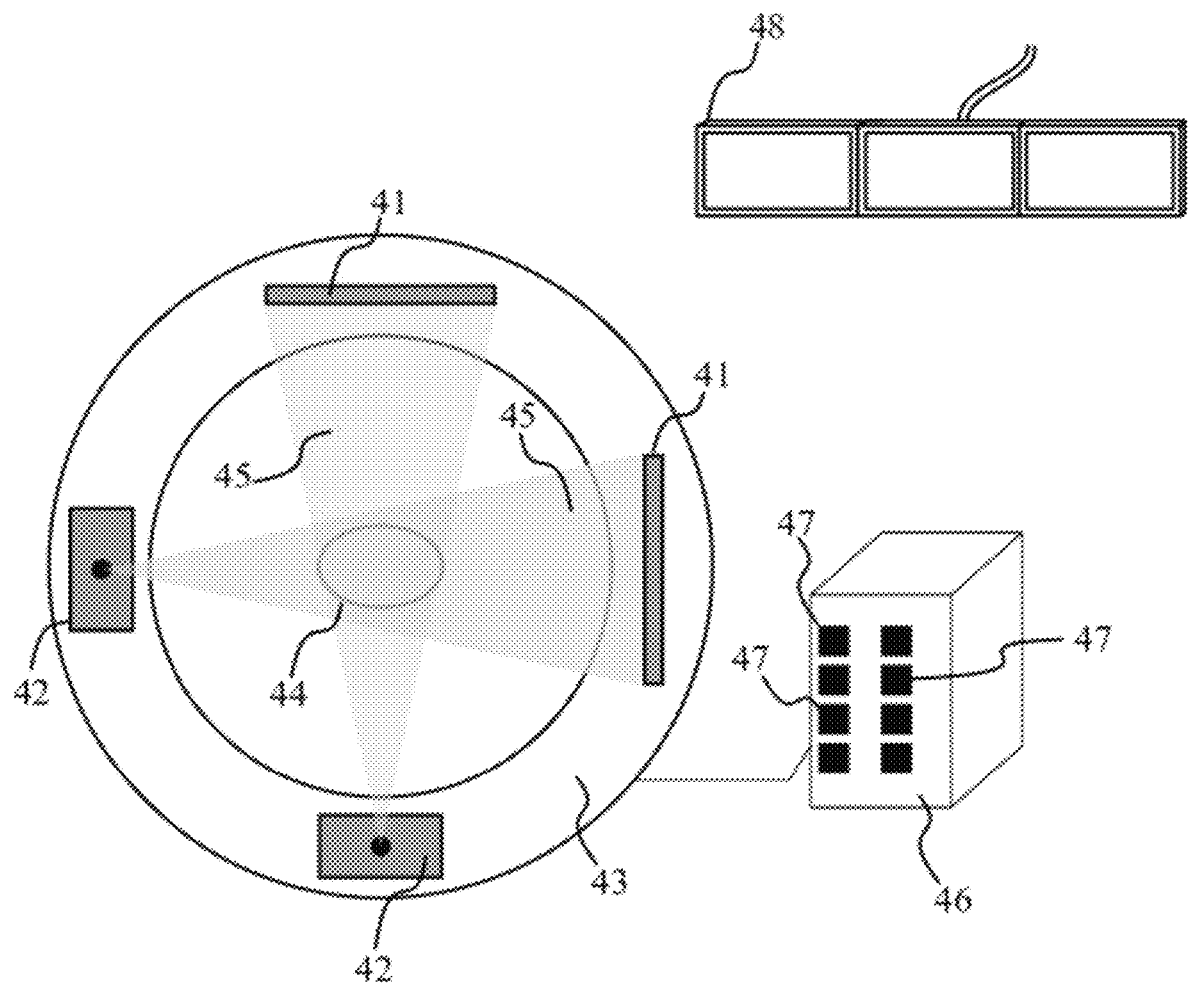
FIG. 4 schematically shows an imaging device which can carry out the methods disclosed herein.

FIG. 4 schematically shows an imaging device which can carry out any of the methods disclosed herein. The imaging device therein contains a rotatably mounted gantry 43, two X-ray generators 42 mounted on this rotatably mounted gantry, and X-ray absorbing flat-panel detectors 41 mounted directly opposite the X-ray generators. The unit comprising an X-ray generator and the flat-panel detector 41 arranged opposite it can be referred to as an image chain. These image chains can be used to provide a first 3D image and 2D update images for the method according to the invention. The various image chains can record the 2D update images simultaneously or pseudo-simultaneously or with a time offset. The region 44 to be examined by means of X-rays 45 may contain anatomical and non-anatomical structures. The computing units 47 required for processing the 2D update images and the first 3D image are integrated into a remote processing unit 46 in FIG. 4. As an alternative, this processing unit 46 or the computing units 47 can be integrated directly into the imaging device. The navigation volume according to the invention can be displayed on an external display unit 48. Alternatively, the display unit may also be mounted directly on the imaging device.

LIST OF REFERENCE NUMBERS

1 First 3D image
2 2D update image
3 Anatomical structures
4 Non-anatomical structures
5 Anatomical model
6 Extraction of the non-anatomical structures
7 First subset
8 Second subset
9 Partial reconstruction
20 Non-anatomical 3D image
11 Anatomical 3D image
12 Navigation volume
13 Extraction of the anatomical structures
14 Determination of the coordinate system
15 Creation of the navigation volume
16 Application of the coordinate transformation
21 Newly recorded 2D update image
31 Removed 2D update image
41 X-ray detector
42 X-ray generator
43 Rotatably mounted gantry
44 Examination zone
45 X-ray beams
46 Processing unit
47 Computing unit
48 Display unit

What is claimed is:

1. A method for operating a medical imaging device for the positionally correct representation of non-anatomical structures during an imaging examination, the method comprising:
   providing a first 3D image which contains at least one anatomical structure;
   extracting at least one anatomical model from the at least one anatomical structure of the first 3D image;
   providing at least two 2D update images captured simultaneously or at different times;
   extracting non-anatomical structures from a first subset of the 2D update images;
   extracting anatomical structures from a second subset of the 2D update images;
   calculating a non-anatomical 3D image from at least two 3D limited projection geometry reconstructions, wherein calculating the non-anatomical 3D image comprises:
      calculating the at least two 3D limited projection geometry reconstructions from the extraction of the non-anatomical structures; and
      removing artifacts from the at least two 3D limited projection geometry reconstructions using a machine learning method;
   reconstructing an anatomical 3D image from the extraction of the anatomical structures;
   registering the anatomical 3D image with the first 3D image by determining a coordinate transformation; and
   creating a navigation volume based on the at least one anatomical model and the non-anatomical 3D image by using the determined coordinate transformation.

2. The method of claim 1, wherein the navigation volume is additionally created based on the anatomical 3D image by using the determined coordinate transformation.

3. The method of claim 1, wherein providing the first 3D image comprises receiving the first 3D image from an X-ray C-arm apparatus, a computer tomography system, or a magnetic resonance tomography system.

4. The method of claim 1, wherein providing the 2D update images comprises receiving the 2D update images from an X-ray C-arm apparatus or a computed tomography system.

5. The method of claim 1, wherein, in the absence of non-anatomical structures in a 2D update image of the first subset, the non-anatomical 3D image is further reconstructed.

6. The method of claim 1, wherein newly acquired 2D update images are added to at least one of the first subset and the second subset, and wherein at least one of the non-anatomical 3D images and the anatomical 3D images are reconstructed at a temporal rate corresponding to a function of an acquisition rate of the 2D update images.

7. The method of claim 1, further comprising, when a new 2D update image has been acquired:
   adding the new 2D update image to the second subset of the provided 2D update images; and
   at least partially reconstructing the anatomical 3D image again in a further reconstruction, wherein all temporally older 2D update images are reused or removed for the further reconstruction.

8. The method of claim 1, wherein the calculation of the non-anatomical 3D image from the at least two 3D limited projection geometry reconstructions is performed by using a machine learning method comprising a neural network.

9. The method of claim 1, further comprising performing a movement correction to correct for movements of a patient having the anatomical structure.

10. The method of claim 1, wherein the extraction of the anatomical and non-anatomical structures from the 2D update images is performed using at least one machine learning method comprising a neural network.

11. The method of claim 1, wherein the non-anatomical 3D image is calculated based at least in part on the 2D update images by using a single machine learning method comprising a neural network.

12. The method of claim 1, wherein the non-anatomical structures extracted from the first subset of the 2D update images comprise non-anatomical structures that belong to a predetermined object class or combination of object classes.

13. The method of claim 1, further comprising separately reconstructing a subset of the non-anatomical structures that belong to a predetermined object class or combination of object classes.

14. The method of claim 1, wherein the non-anatomical structures comprise at least one of a guide wire and a catheter.

15. A gantry-based medical imaging system for carrying out an imaging examination and representation of non-anatomical structures, the device comprising:
- a provisioning unit configured to provide a first 3D image, the first 3D image including at least one anatomical structure;
- at least two image chains configured to record at least one of 2D update images and 3D images;
- a computing unit comprising one or more processors configured by computer-executable instructions stored in the computing unit to at least:
  - extract an anatomical model from the at least one anatomical structure in the first 3D image;
  - extract anatomical and non-anatomical structures from the 2D update images;
  - calculate 3D limited projection geometry reconstructions from the extraction of non-anatomical structures;
  - calculate a non-anatomical 3D image from at least two of the 3D limited projection geometry reconstructions, wherein calculating the non-anatomical 3D image comprises removing artifacts from the at least two 3D limited projection geometry reconstructions using a machine learning method;
  - calculate an anatomical 3D image from the extraction of anatomical structures; and
  - create a navigation volume from the anatomical model and the non-anatomical 3D image by determining a coordinate transformation, wherein the coordinate transformation causes the anatomical model to be positioned correctly in the navigation volume; and
- a display configured to display the navigation volume.

* * * * *